US012642446B2

(12) United States Patent
Yan

(10) Patent No.: US 12,642,446 B2
(45) Date of Patent: Jun. 2, 2026

(54) PPG SENSOR, PPG DETECTION METHOD, AND ELECTRONIC DEVICE

(71) Applicant: GUANGDONG OPPO MOBILE TELECOMMUNICATIONS CORP., LTD., Dongguan (CN)

(72) Inventor: Rui Yan, Dongguan (CN)

(73) Assignee: GUANGDONG OPPO MOBILE TELECOMMUNICATIONS CORP., LTD., Dongguan (CN)

( * ) Notice: Subject to any disclaimer, the term of this patent is extended or adjusted under 35 U.S.C. 154(b) by 408 days.

(21) Appl. No.: 18/133,793

(22) Filed: Apr. 12, 2023

(65) Prior Publication Data

US 2023/0248252 A1 Aug. 10, 2023

Related U.S. Application Data

(63) Continuation of application No. PCT/CN2021/112439, filed on Aug. 13, 2021.

(30) Foreign Application Priority Data

Oct. 15, 2020 (CN) .......................... 202011101546.8

(51) Int. Cl.
$A61B \ 5/024$ (2006.01)
$A61B \ 5/00$ (2006.01)
$A61B \ 5/026$ (2006.01)

(52) U.S. Cl.
CPC ........ A61B 5/02427 (2013.01); A61B 5/0261 (2013.01); A61B 5/681 (2013.01); *A61B 2562/043* (2013.01); *A61B 2562/046* (2013.01)

(58) Field of Classification Search
None
See application file for complete search history.

(56) References Cited

U.S. PATENT DOCUMENTS

2017/0000350 A1* 1/2017 Kwon ................ A61B 5/02427
2017/0105638 A1 4/2017 Kulach
(Continued)

FOREIGN PATENT DOCUMENTS

CN 103002799 A 3/2013
CN 105208924 A 12/2015
(Continued)

OTHER PUBLICATIONS

Chinese First Office Action and search report in the corresponding Chinese Patent Application No. 202011101546.8, mailed Aug. 1, 2023.

(Continued)

*Primary Examiner* — Michael J Carey
*Assistant Examiner* — Marjan Saboktakin
(74) *Attorney, Agent, or Firm* — Ladas & Parry, LLP

(57) ABSTRACT

A PPG sensor, an electronic device, and a wearable device are provided. The PPG sensor includes: a first light-emitting unit, configured to emit a first optical signal; a second light-emitting unit, configured to at least emit another first optical signal; and a plurality of photoelectric sensors, wherein the first light-emitting unit and M photoelectric sensors of the plurality of photoelectric sensors form a first measurement channel, the M photoelectric sensors are connected in parallel, and a first photocurrent signal is obtained based on the first measurement channel; the second light-emitting unit and N photoelectric sensors of the plurality of photoelectric sensors form a second measurement channel, the N photoelectric sensors are connected in parallel, and a second photocurrent signal is obtained based on the second measurement channel; wherein N is greater than M, and both M and N are natural numbers.

20 Claims, 8 Drawing Sheets

(56)                    References Cited

U.S. PATENT DOCUMENTS

2019/0090766 A1*   3/2019   Block ................... H10F 77/413
2019/0360928 A1*   11/2019  Lasarov ............. A61B 5/02416
2021/0161413 A1    6/2021   Ng et al.

FOREIGN PATENT DOCUMENTS

| CN | 105380634 | A | 3/2016 |
| CN | 106308776 | A | 1/2017 |
| CN | 106357879 | A | 1/2017 |
| CN | 106725323 | A | 5/2017 |
| CN | 108606801 | A | 10/2018 |
| CN | 108652605 | A | 10/2018 |
| CN | 109640794 | A | 4/2019 |
| CN | 110179438 | A | 8/2019 |
| CN | 111094941 | A | 5/2020 |
| CN | 111132610 | A | 5/2020 |
| CN | 111493846 | A | 8/2020 |
| CN | 215457944 | U | 1/2022 |
| JP | 2004349938 | A | 12/2004 |
| RU | 2543616 | C2 | 3/2015 |
| WO | 2018002442 | A1 | 1/2018 |
| WO | 2019237281 | A1 | 12/2019 |

OTHER PUBLICATIONS

Chinese Notification to Grant Patent Right for Invention, Chinese Application No. 202011101546.8, mailed May 13, 2024 (6 pages).
India First Office Action, India Patent Application No. 202317030962, mailed Jun. 27, 2024 (6 pages).
European Search Report from the corresponding European Patent Application No. 21879091.3, mailed Feb. 15, 2024 (17 pages).
International Search Report (ISR) dated Nov. 19, 2021 for Application No. PCT/CN2021/112439, and its English translation provided by WIPO.
Written Opinion (WOSA) dated Nov. 19, 2021 for Application No. PCT/CN2021/112439, and its English translation provided by WIPO.
European Examination Report from corresponding European Application No. 21879091.3, mailed Aug. 12, 2025 (5 pages).

* cited by examiner driving a first light-emitting unit to emit a first optical signal, and obtaining a first photocurrent signal by controlling M photoelectric sensors in a first measurement channel to be connected in parallel; or driving a second light-emitting unit to emit the first optical signal, and obtaining a second photocurrent signal by controlling N photoelectric sensors in a second measurement channel to be connected in parallel ; wherein N is greater than M, and both M and N are natural numbers greater than 1 ~1302 determining a target measurement channel from the first measurement channel and the second measurement channel according to the obtained photocurrent signal ~1304 driving the target measurement channel to detect the biological characteristics of an object to be detected ~1306

FIG. 13 driving the second light-emitting unit to emit a second optical signal, and obtaining a plurality of third photocurrent signals by controlling the plurality of photoelectric sensors in a time-sharing mode ~1402 obtaining a heart-rate detection result according to each of the plurality of third photocurrent signals ~1404 detecting heart-rate information of the object to be detected according to the heart-rate detection result ~1406

FIG. 14

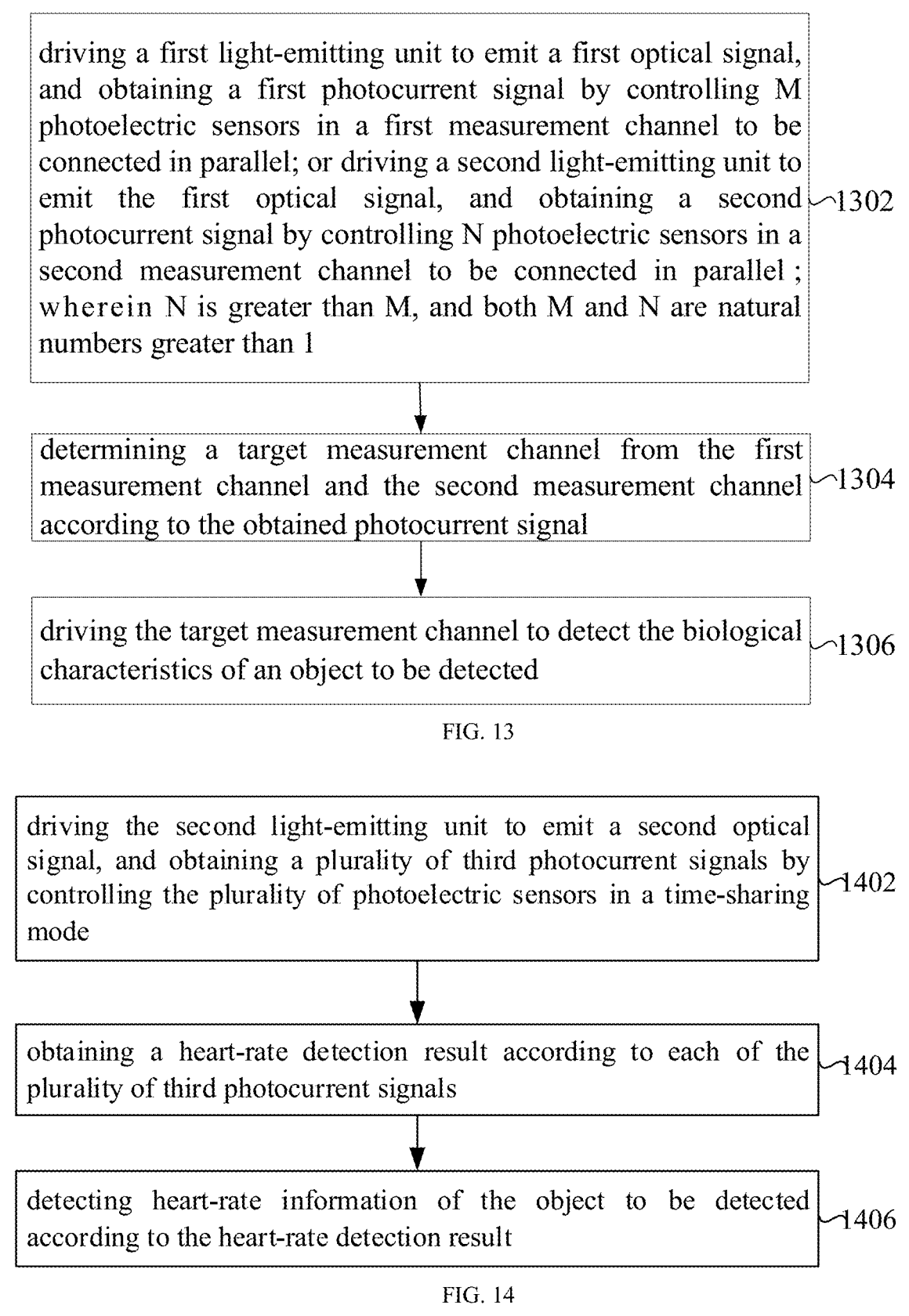

PPG SENSOR, PPG DETECTION METHOD, AND ELECTRONIC DEVICE

CROSS REFERENCE TO RELATED APPLICATIONS

The present disclosure is a continuation of International Patent Application No. PCT/CN2021/112439, filed on Aug. 13, 2021, which claims priority to Chinese Patent Application No. 202011101546.8 entitled "PPG SENSOR, PPG DETECTION METHOD, ELECTRONIC DEVICE, AND WEARABLE DEVICE", filed on Oct. 15, 2020 in the National Intellectual Property Administration of China, the disclosures of which are herein incorporated by reference in their entireties.

TECHNICAL FIELD

The present disclosure relates to wearable devices, and in particular to a photoplethysmography (PPG) sensor, a PPG detection method, and an electronic device.

BACKGROUND

The statements herein only provide background information relevant to the present disclosure and do not necessarily form exemplary prior art.

A wearable device may be provided with a photoplethysmography (PPG) sensor, and measure physiological parameter information, such as heart rates and blood oxygen saturation, and the like, based on the PPG technology. There are two kinds of PPG detection technologies in view of layout of the PPG sensor, one is the transmission-mode detection technology, and the other is the reflection-mode detection technology. The PPG sensor applied in the wearable device generally uses the reflection-mode detection technology to measure the physiological parameter information at the wrist. The power-consumption level of the existing PPG sensor is high.

SUMMARY

Various embodiments of the present disclosure provide a photoplethysmography (PPG) sensor, an electronic device, and a wearable device.

Some embodiments of the present disclosure provide a PPG sensor. The photoplethysmography (PPG) sensor includes:

a first light-emitting unit, configured to emit a first optical signal;

a second light-emitting unit, configured to at least emit another first optical signal;

a plurality of photoelectric sensors, wherein the first light-emitting unit and M photoelectric sensors of the plurality of photoelectric sensors form a first measurement channel, the M photoelectric sensors are connected in parallel, and a first photocurrent signal is obtained based on the first measurement channel; the second light-emitting unit and N photoelectric sensors of the plurality of photoelectric sensors form a second measurement channel, the N photoelectric sensors are connected in parallel, and a second photocurrent signal is obtained based on the N photoelectric sensors; wherein N is greater than M, and less than or equal to the total number of the plurality of photoelectric sensors, and both M and N are natural numbers and a control module, connected to the first light-emitting unit, the second light-emitting unit, and the plurality of photoelectric sensors respectively, and configured to determine a target measurement channel according to the first photocurrent signal or the second photocurrent signal received by the control module and control the target measurement channel to detect biological characteristics of an object to be detected.

Some embodiments of the present disclosure provide a PPG detection method. The photoplethysmography (PPG) detection method includes:

driving a first light-emitting unit to emit a first optical signal, and obtaining a first photocurrent signal by controlling M photoelectric sensors in a first measurement channel to be connected in parallel; or driving a second light-emitting unit to emit another first optical signal, and obtaining a second photocurrent signal by controlling N photoelectric sensors in a second measurement channel to be connected in parallel; wherein N is greater than M, and both M and N are natural numbers;

determining a target measurement channel from the first measurement channel and the second measurement channel according to the first photocurrent signal or the second photocurrent signal; and driving the target measurement channel to detect biological characteristics of an object to be detected.

Some embodiments of the present disclosure provide an electronic device. The electronic device includes:

a housing, defining a detection window; and a photoplethysmography (PPG) sensor exposed out of the housing from the detection window, the PPG sensor includes:

a first light-emitting unit, configured to emit a first optical signal;

a second light-emitting unit, configured to at least emit another first optical signal;

a plurality of photoelectric sensors, wherein the first light-emitting unit and M photoelectric sensors of the plurality of photoelectric sensors form a first measurement channel, the M photoelectric sensors are connected in parallel, and a first photocurrent signal is obtained based on the first measurement channel; the second light-emitting unit and N photoelectric sensors of the plurality of photoelectric sensors form a second measurement channel, the N photoelectric sensors are connected in parallel, and a second photocurrent signal is obtained based on the second measurement channel; wherein N is greater than M, and less than or equal to the total number of the plurality of photoelectric sensors, and both M and N are natural numbers; and a control module, connected to the first light-emitting unit, the second light-emitting unit, and the plurality of photoelectric sensors respectively, and configured to determine a target measurement channel according to the first photocurrent signal or the second photocurrent signal received by the control module and control the target measurement channel to detect biological characteristics of an object to be detected.

The details of one or more embodiments of the present disclosure are set out in the following figures and description. Other features, purposes and advantages of the present disclosure will become apparent from the description, figures, and claims.

BRIEF DESCRIPTION OF THE DRAWINGS

In order to more clearly explain the technical solutions of the embodiments of the present disclosure or the related art, the following will briefly introduce the figures needed in the description of the embodiments or the related art. It is obvious that the figures in the following description are only some embodiments of the present disclosure. For those skilled in the art, other figures may be obtained from these figures without any creative work.

FIG. 13 is a schematic flow chart of a PPG detection method in some embodiments of the present disclosure.

FIG. 14 is a further schematic flow chart of the PPG detection method in some embodiments of the present disclosure.

DETAILED DESCRIPTIONS

In order to make the purpose, technical solutions, and advantages of the present disclosure clearer, the present disclosure will be further described in detail with the attached figures and embodiments. It should be understood that the embodiments described herein are only used to explain the present disclosure, but not to limit the present disclosure.

It can be understood that, the terms "first", "second" and the like used in the present disclosure may be used to describe various elements herein, while these elements are not limited by these terms. These terms are only used to distinguish a first element from the other elements. For example, without departing from the scope of the present disclosure, a first light-emitting unit may be called a second light-emitting unit, and similarly, the second light-emitting unit may be called the first light-emitting unit. Both the first light-emitting unit and the second light-emitting unit are light-emitting assemblies, but they are not the same light-emitting assembly.

In addition, the terms "first" and "second" are only used for describing purposes, and cannot be understood as indicating or implying relative importance or implying the number of technical features indicated. Therefore, the features defined with "first" and "second" may include at least one of these features explicitly or implicitly. In the description of the present disclosure, "a plurality of" means at least two, such as two, three, etc., unless otherwise specified. In the description of the present disclosure, "several" means at least one, such as one, two, etc., unless otherwise specified.

Figure 1:
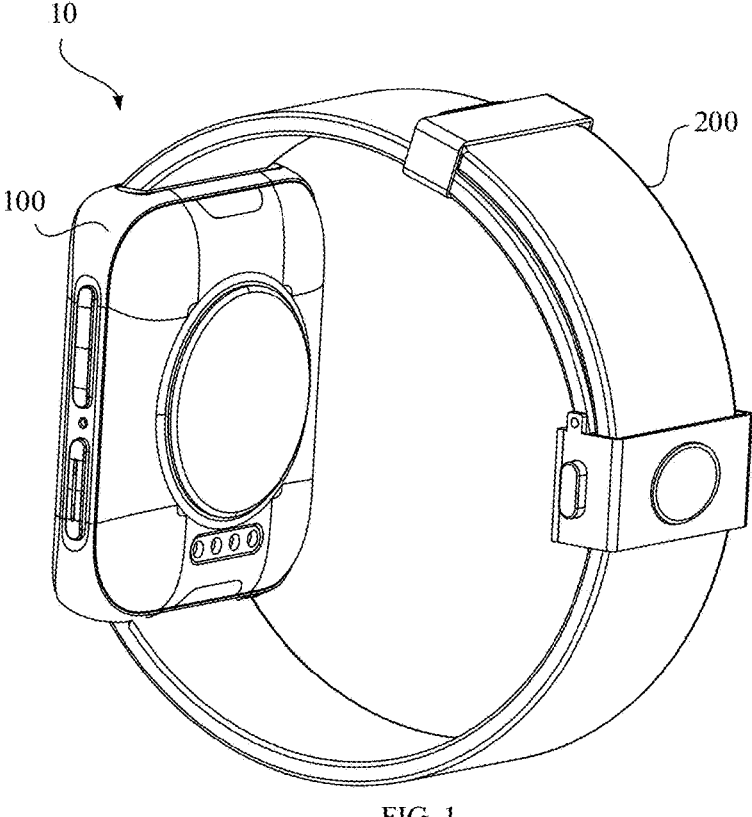
FIG. 1 is a schematic perspective view of a wearable device in some embodiments of the present disclosure.
Figure 2:
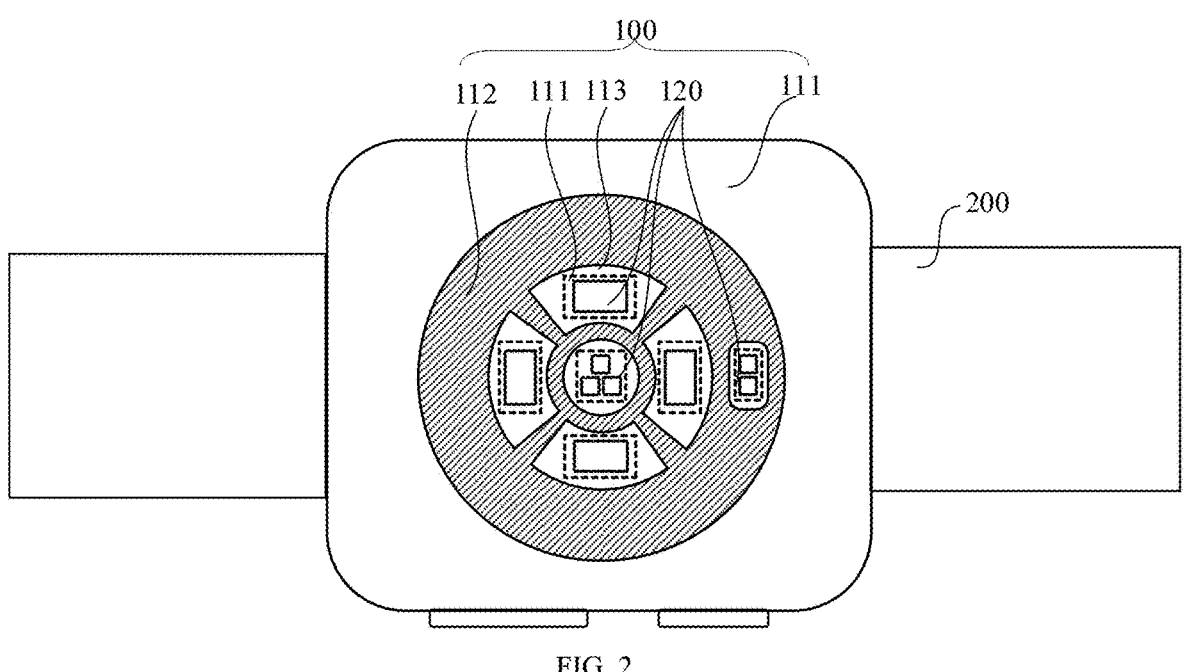
FIG. 2 is a schematic planar view of the wearable device in some embodiments of the present disclosure.

As shown in FIG. 1, in some embodiments, the wearable device 10 includes an electronic device 100 and a strap assembly 200. The electronic device 100 is mounted to the strap assembly 200 and may be worn to the wrist of a user through the strap assembly 200, that is, the strap assembly 200 may fasten the electronic device 100 at a wearing position (such as the wrist, the ankle, the head, and soon) of the user. As shown in FIG. 2, the electronic device 100 includes a housing 110 and electronic components (such as a circuit board, a battery, and so on) arranged in the housing 110. The housing 110 has a mounting cavity. The electronic components (such as the circuit board, the battery, and so on) are arranged in the mounting cavity. The housing 110 may be made of non-metallic materials, such as plastic, rubber, silicone, wood, ceramics, glass, and so on. The housing 110 may also be made of metal materials, such as stainless steel, aluminum alloy, magnesium alloy, and so on. The housing 110 may also be a metal injection-molded element. Metal materials are used to ensure the structural rigidity of the housing 110. The internal surface of the metal body is injection-molded to form structures for assembly and positioning, such as a protrusion, a groove, a threaded hole, and so on.

Figure 3A:
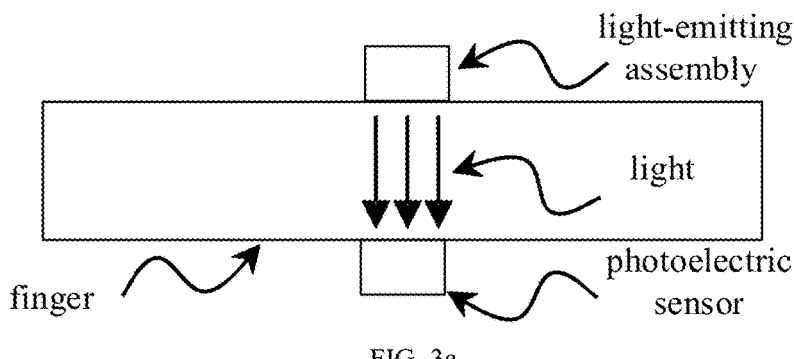
FIG. 3a is a schematic view illustrating the PPG transmission-mode detection technology in some embodiments of the present disclosure.
Figure 3B:
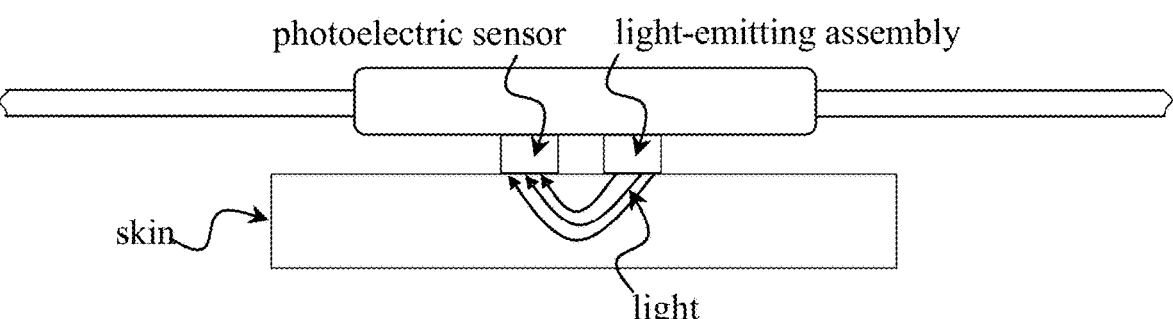
FIG. 3b is a schematic view illustrating the PPG reflection-mode detection technology in some embodiments of the present disclosure.

The housing 110 has a detection window 111. The detection window 111 is configured to transmit light, so as to transmit optical signals emitted and reflected by the electronic components built in the housing 110. In this way, vital sign signals (such as the heart rate, the blood oxygen saturation, and so on) of a human body may be detected. The electronic components include for example a PPG sensor 120. There are two kinds of PPG detection technologies in view of layout of the PPG sensor 120: one is the transmission-mode detection technology, the other is the reflection-mode detection technology. As shown in FIG. 3a, the transmission-mode detection technology may trace and record, based on differences of intensities of the transmitted light, changes of a vascular volume during a cardiac cycle, and obtain the heart rate, the blood oxygen saturation or etc. As shown in FIG. 3b, the reflection-mode detection technology may trace and record, based on the differences of intensities of the reflected light, changes of the vascular volume during a cardiac cycle, and obtain vital signs such as heart rates, blood oxygen saturation, etc. By incorporating the PPG sensor 120 provided in some embodiments of the present disclosure to the wearable device 10, the user may conveniently detect his/her heart rates and blood oxygen saturation, etc. anytime and anywhere. In this way, not only functions of the wearable electronic device are enriched, but also health needs of the user are greatly satisfied.

As shown in FIG. 2, in some embodiments, the housing 110 may include a light barrier (also called as "opaque baffle wall") 112 and a transparent window 113. The size of the light barrier 112 matches the size of the detection window 111, to prevent optical crosstalk between the light-emitting assemblies of the PPG sensor 120 and a photoelectric sensor. The transparent window 113 is overlaid on and covers the detection window 111 for waterproof and dustproof and increase the light transmittance of the PPG sensor 120.

In some embodiments, the wearable device 10 is a smart watch or a bracelet. The electronic components, such as the battery, the circuit board, the display screen module, the PPG sensor 120, and the like, are arranged in the mounting cavity. Electronic components such as a processor, a storage unit, a communication module, and the like of the wearable device 10 may be integrated on the circuit board. The battery may supply power to the circuit board, the display screen module, and other electronic components.

The housing 110 may be substantially in the shape of a rectangular frame. The four corners of the rectangle may be chamfered into arcs. In this way, the appearance characteristics of the wearable device 10 may be improved. In some embodiments, the housing 110 may be substantially in the shape of a circular frame. The side surface of the housing 110 may be arranged with a matching or mating structure to mount the strap assembly 200. The strap assembly 200 may be reliably connected to the housing 110 through the matching or mating structure of the housing 110, such that the electronic device 100 is reliably worn on the hand of the user. In some embodiments, the strap assembly 200 may be easily removed or detached from the housing 110, in this way, the user may be allowed to easily change the strap assembly 200. For example, the user may purchase variety styles of strap assemblies 200, and change the strap assembly 200 according to usage scenarios to improve the convenience of use. For example, the user may use a relatively formal strap assembly 200 in formal occasions, and use a strap assembly 200 of a casual style in casual and entertainment occasions.

Figure 4:
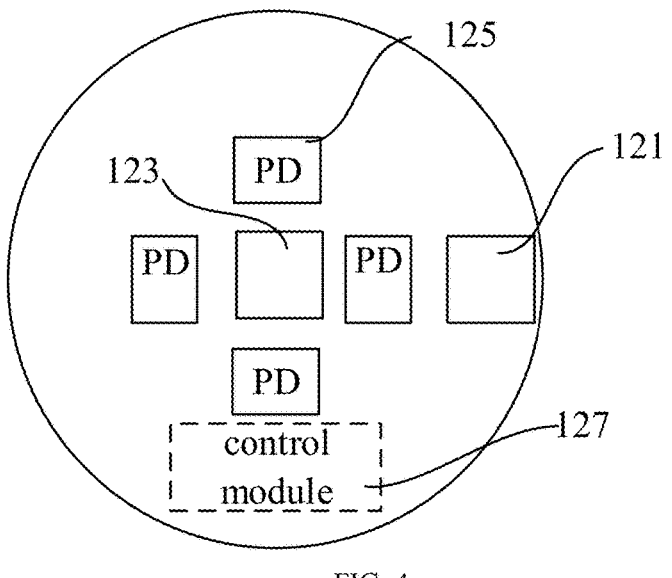
FIG. 4 is a schematic diagram illustrating a first frame structure of a PPG sensor in some embodiments of the present disclosure.

As shown in FIG. 4, in some embodiments, the PPG sensor includes a first light-emitting unit 121, a second light-emitting unit 123, a plurality of photoelectric sensors 125, and a control module 127. The first light-emitting unit 121 may be configured to receive a drive signal to emit a first optical signal, and the second light-emitting unit 123 may be configured to receive a drive signal to emit another first optical signal. Each of the first optical signal and the another first optical signal may include at least one selected from the group consisting of red light and infrared light for detecting the blood oxygen saturation. The first light-emitting unit 121 and the second light-emitting unit 123 may include one or more light-emitting diodes (LEDs). In some embodiments, the one or more LEDs may include a red-light LED, an infrared-light LED, or a green-light LED. In some embodiments, each of the first light-emitting unit 121 and the second light-emitting unit 123 may include any one selected from the group consisting of an LED assembly including a red-light LED or an infrared-light LED, a two-in-one LED assembly emitting both the red light and the infrared light, and a three-in-one LED assembly emitting the green light, the red light, and the infrared light.

In some embodiments, the second light-emitting unit 123 may also be configured to emit a second optical signal. The second optical signal may include a green light for detecting heart-rate information. The second light-emitting unit 123 may include one or more LEDs. In some embodiments, the one or more LEDs may include at least a green-light LED. In some embodiments, the second light-emitting unit 123 may include any one selected from the group consisting of a two-in-one LED assembly emitting both the green light and the red light, a two-in-one LED assembly emitting both the green light and the infrared light, and a three-in-one LED assembly emitting both the green light, the red light, and the infrared light.

Each of the plurality of photoelectric sensors 125 may work in a zero-bias condition. That is, each of the plurality of photoelectric sensors 125 may be a photodiode (PD) in a photovoltaic mode, and may be configured to convert a received optical signal into a photocurrent signal. The plurality of photoelectric sensors 125 may be divided into a plurality of photoelectric sensor groups. The photoelectric sensors 125 in each of the plurality of photoelectric sensor groups may be connected in parallel. Each of the plurality of photoelectric sensor groups may form a measurement channel with the first light-emitting unit 121 or the second light-emitting unit 123 respectively, so as to detect the biological characteristics of an object to be detected. In some embodiments, the first light-emitting unit 121 and a first photoelectric sensor group may form a first measurement channel, and a first photocurrent signal may be obtained based on the first photoelectric sensor group forming the first measurement channel. The first photoelectric sensor group may include M photoelectric sensors 125 connected in parallel. The second light-emitting unit 123 and a second photoelectric sensor group may form a second measurement channel, and a second photocurrent signal may be obtained based on the second photoelectric sensor group forming the second measurement channel. The second photoelectric sensor group may include N photoelectric sensors 125 connected in parallel. M is less than N, and both M and N are natural numbers greater than 1. The first photoelectric sensor group may share one or more photoelectric sensors 125 with the second photoelectric sensor group. It should be noted that, the total number of the photoelectric sensors 125 included in the PPG sensor is greater than or equal to N.

The control module 127 is connected to the first light-emitting unit 121, the second light-emitting unit 123, and the plurality of photoelectric sensors 125 respectively. The control module 127 may be configured to control the first measurement channel or the second measurement channel to obtain a corresponding PPG signal. In some embodiments, in case that the control module 127 drives the first light-emitting unit 121 to emit the first optical signal, a first PPG signal may be obtained based on the first photocurrent signal acquired by the first photoelectric sensor group in the constructed first measurement channel. In some embodiments, in case that the control module 127 drives the second light-emitting unit 123 to emit the first optical signal, a second PPG signal may be obtained based on the second photocurrent signal acquired by the second photoelectric sensor group in the constructed second measurement channel.

In some embodiments, the control module 127 may determine a target measurement channel from the first measurement channel and the second measurement channel according to the PPG signal obtained from any one of the measurement channels, and then control the target measurement channel to obtain the biological characteristics of the object to be detected, such as blood oxygen saturation, etc. In some embodiments, in case that the first measurement channel is currently controlled to work, that is, the first light-emitting unit 121 emits the first optical signal and the M photoelectric sensors 125 in the first photoelectric sensor group is controlled to be connected in parallel to acquire the first photocurrent signal, whether the target measurement channel is the first measurement channel or the second measurement channel may be determined according to the first PPG signal obtained by the first measurement channel.

In case that the target measurement channel is the first measurement channel, the first measurement channel is kept in a working state. In case that the target measurement channel is the second measurement channel, the second measurement channel is controlled to be in a working state. That is, the second light-emitting unit 123 is controlled to emit the another first optical signal and the N photoelectric sensors 125 in the second photoelectric sensor group is controlled to be connected in parallel to acquire the second photocurrent signal. In this way, the control module 127 may obtain the second PPG signal according to the second photocurrent signal to detect the blood oxygen saturation of the object to be detected.

The PPG sensor includes the first light-emitting unit 121, the second light-emitting unit 123, the plurality of photoelectric sensors 125, and the control module 127. The first measurement channel may be constructed based on or by using the M photoelectric sensors 125 connected in parallel and the first light-emitting unit 121. The second measurement channel may be constructed based on or by using the N photoelectric sensors 125 connected in parallel and the second light-emitting unit 123. In this way, each of the first measurement channel and the second measurement channel includes a plurality of photoelectric sensors 125 connected in parallel, and the power consumption of the PPG sensor may be reduced. In addition, the numbers of the photoelectric sensors 125 connected in parallel in the first measurement channel and the second measurement channel are different from each other, and the power-consumption levels corresponding to the first measurement channel and the second measurement channel are also different from each other. The PPG sensor may determine the target measurement channel according to the first photocurrent signal or the second photocurrent signal currently acquired, so as to adapt to different detection scenarios. On condition that the photocurrent signals of the same degree are acquired, the greater the number of the photoelectric sensors 125 connected in parallel in the measurement channel, the smaller the drive voltage or drive current used to drive the first light-emitting unit 121 or the second light-emitting unit 123, and the lower the power consumption of the PPG sensor. In some embodiments, in case that the PPG signal corresponding to the first photocurrent signal or the second photocurrent signal is relatively weak, the first measurement channel with a high power-consumption level may be configured to detect the biological characteristics. In case that the PPG signal corresponding to the first photocurrent signal or the second photocurrent signal is relatively strong, the second measurement channel with a low power-consumption level may be configured to detect the biological characteristics. In this way, not only the accuracy of measurement is ensured, but also the power consumption is taken into account.

In some embodiments, a first distance is defined between the first light-emitting unit 121 and each of the photoelectric sensors 125 in the first measurement channel, and first distances corresponding to the photoelectric sensors 125 in the first measurement channel are substantially equal to each other. A second distance is defined between the second light-emitting unit 123 and each of the photoelectric sensors 125 in the second measurement channel, and second distances corresponding to the photoelectric sensors 125 in the second measurement channel are substantially equal to each other. The first distance is greater than the second distance. The distance between the first light-emitting unit 121 and any one of the photoelectric sensors 125 may be understood as the distance between the center position of the first light-emitting unit 121 and the center position of any one of the photoelectric sensors 125. The distance between the second light-emitting unit 123 and any one of the photoelectric sensors 125 may be understood as the distance between the center position of the second light-emitting unit 123 and the center position of any one of the photoelectric sensors 125. The center position may be understood as the geometric center of each component.

Figures 5, 6:
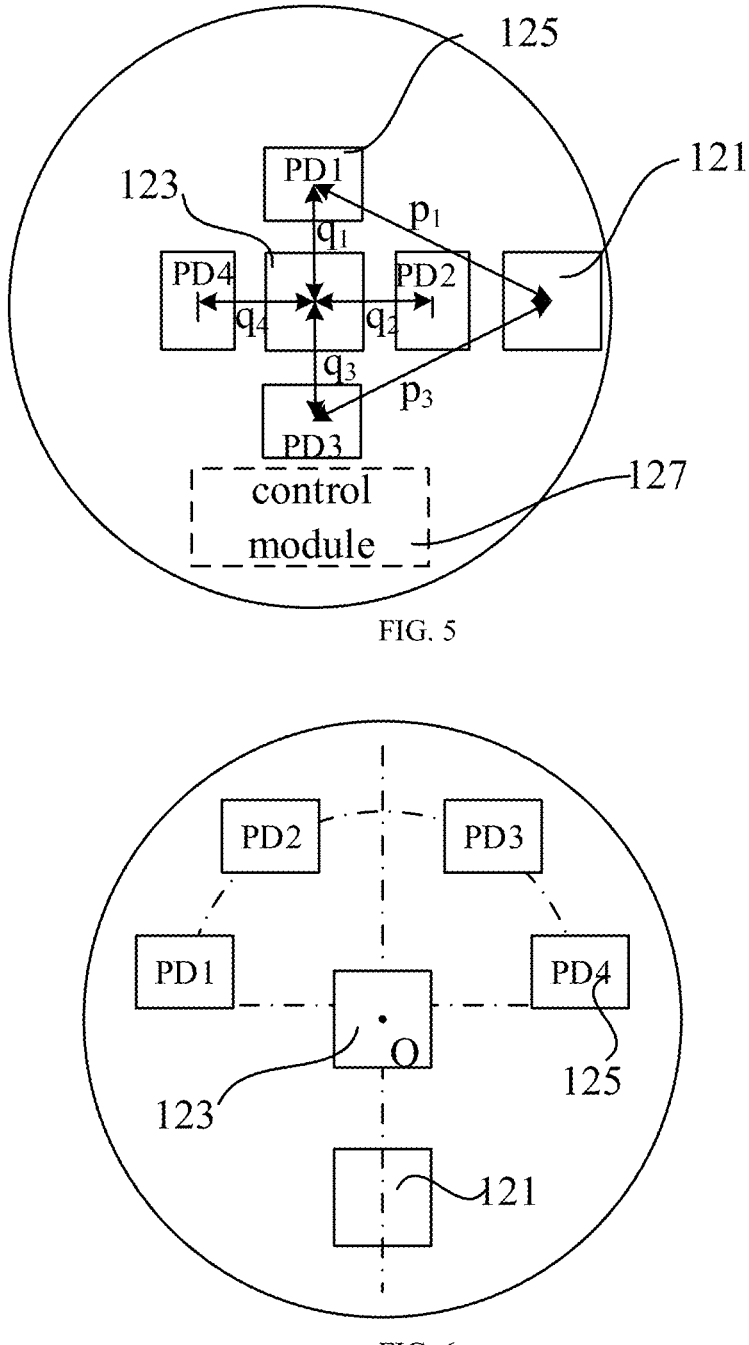
FIG. 5 is a schematic diagram illustrating a second frame structure of the PPG sensor in some embodiments of the present disclosure.
FIG. 6 is a schematic diagram illustrating a third frame structure of the PPG sensor in some embodiments of the present disclosure.

As shown in FIG. 5, in some embodiments, in case that the number of the plurality of photoelectric sensors 125 is J, the plurality of photoelectric sensors 125 may be recorded as PD1, PD2, PD3, . . . , and PDj, respectively. M photoelectric sensors 125 at the same distances from the first light-emitting unit 121 are selected from the J photoelectric sensors 125, and the M photoelectric sensors 125 are selected as the first photoelectric sensor group. The M photoelectric sensors 125 are connected in parallel under the control of the control module 127, and M is less than J. The distance between the first light-emitting unit 121 and each of the photoelectric sensors 125 in the first photoelectric sensor group may be recorded as the first distance $p_i$. In some embodiments, the photoelectric sensors 125 in the first photoelectric sensor group may include the PD1 and the PD3, and p1=p3. N photoelectric sensors 125 at the same distances from the second light-emitting unit 123 are selected from the J photoelectric sensors 125, and the N photoelectric sensors 125 are selected as the second photoelectric sensor group. The N photoelectric sensors 125 are connected in parallel under the control of the control module 127, M is less than J, and M<N≤J. The distance between the second light-emitting unit 123 and each of the photoelectric sensors 125 in the second photoelectric sensor group may be recorded as the second distance qi. In some embodiments, the photoelectric sensors 125 in the second photoelectric sensor group include PD1, PD2, PD3, and PD4, and q1=q2=q3=q4. The first distance is greater than the second distance, that is, pi>qi. Since the first distance in the first measurement channel is greater than the second distance in the second measurement channel, compared with using the second measurement channel, using the first measurement channel (which has a greater distance) may obtain a better PPG signal, and detect the blood-oxygen-saturation information of the object to be detected more accurately. While the number of the photoelectric sensors 125 in the first measurement channel is less than the number of the photoelectric sensors 125 in the second measurement channel, the power consumption of the second measurement channel is lower than the first measurement channel.

The blood-oxygen-saturation information is detected by arranging two measurement channels with different power-consumption levels, in this way, according to the current usage scenario of the user, the target measurement channel matching the scenario may be intelligently selected to detect the blood-oxygen-saturation information of the user, the flexibility of the PPG sensor may be improved, and the power consumption and performance may be optimized. In some embodiments, in harsh environments, such as low temperature (the lower the ambient temperature, the weaker the PPG signal of the human body), as the user needs to detect the blood oxygen saturation, the PPG sensor may use the first measurement channel with the high power-consumption level and a high detection accuracy to detect the blood oxygen saturation for a single time, so as to obtain the blood oxygen saturation of the object to be detected accurately. In some embodiments, in continuously measuring the blood oxygen saturation during sleep (the PPG signal of the human body is relatively strong in this case), the PPG sensor may use the second measurement channel with the low power-consumption level for continuous measurement of the blood oxygen saturation to obtain the blood oxygen saturation of the object to be detected accurately. In this way, not only the accuracy of the measurement is ensured, but also the power consumption is taken into account.

As shown in FIG. 6, in some embodiments, the plurality of photoelectric sensors 125 are arranged along the same arc and spaced apart from each other. Both the first light-emitting unit 121 and the second light-emitting unit 123 are arranged on the same side of the arc. In some embodiments, the plurality of photoelectric sensors 125 may include the PD1, the PD2, the PD3, and the PD4, and the PD1, the PD2, the PD3, and the PD4 are sequentially arranged along the same arc and spaced apart from each other. The first light-emitting unit 121 and the second light-emitting unit 123 may be arranged on the same side of the arc. The arc may be understood as a circular arc, and the second light-emitting unit 123 may be located at the center position of the circular arc.

Figures 7, 8:
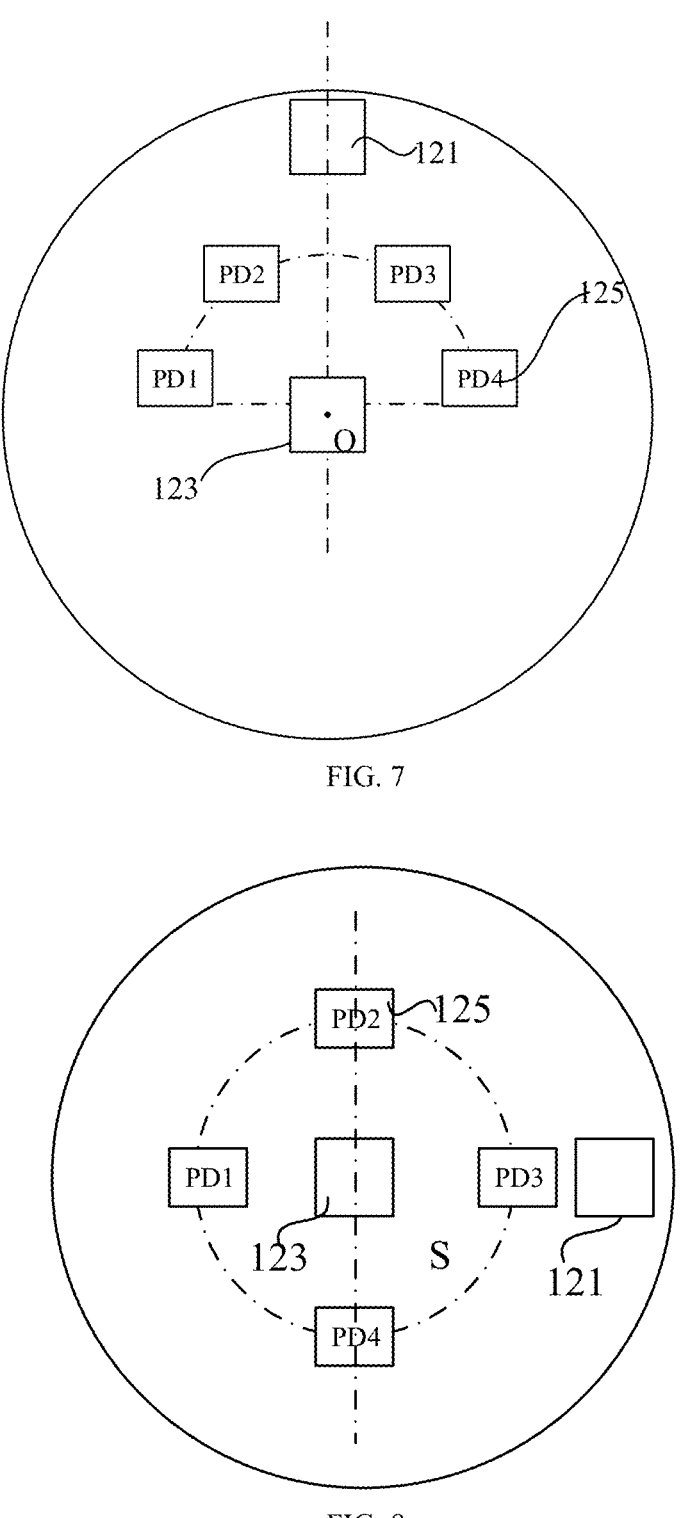
FIG. 7 is a schematic diagram illustrating a fourth frame structure of the PPG sensor in some embodiments of the present disclosure.
FIG. 8 is a schematic diagram illustrating a fifth frame structure of the PPG sensor in some embodiments of the present disclosure.

As shown in FIG. 7, in some embodiments, the plurality of photoelectric sensors 125 are arranged along the same arc and spaced apart from each other. The first light-emitting unit 121 and the second light-emitting unit 123 are arranged on different sides of the arc respectively. In some embodiments, the plurality of photoelectric sensors 125 may include the PD1, the PD2, the PD3, and the PD4, and the PD1, the PD2, the PD3, and the PD4 are sequentially arranged along the same arc and spaced apart from each other. The arc may be understood as a circular arc. The second light-emitting unit 123 may be located at the center position of the circular arc, and the first light-emitting unit 121 may be arranged at the side of the circular arc away from the center position.

As for the PPG sensor shown in FIG. 6 and FIG. 7, the first light-emitting unit 121 and the second light-emitting unit 123 are located in the same straight line. The straight line may be understood as the perpendicular bisector of the PD2 and the PD3. The distance between the first light-emitting unit 121 and the PD2 and the distance between the first light-emitting unit 121 and the PD3 are substantially equal to each other, and the PD2 and the PD3 may form the first photoelectric sensor group; or the distance between the first light-emitting unit 121 and the PD1 and the distance between the first light-emitting unit 121 and the PD4 are substantially equal to each other, and the PD1 and the PD4 may form the first photoelectric sensor group. The distances between the second light-emitting unit 123 and the PD1, the PD2, the PD3, and the PD4 are substantially equal to each other, and the PD1, the PD2, the PD3, and the PD4 may form the second photoelectric sensor group.

It should be noted that, the plurality of photoelectric sensors 125 may be arranged along the same arc at equal or unequal intervals. The centers of the plurality of photoelectric sensors 125 may be located in the same arc, while certain engineering errors or allowable errors may be allowed.

As shown in FIG. 8, in some embodiments, the plurality of photoelectric sensors 125 are arranged in an array. The array may be a rectangular array or a circular array. The second light-emitting unit 123 is located in the center position of the array, and the first light-emitting unit 121 is arranged out of the area S in which the array is located, that is, arranged in an area beyond the area S. In some embodiments, the plurality of photoelectric sensors 125 may include four photoelectric sensors 125, which may be recorded as PD1, PD2, PD3, and PD4. The PD1, the PD2, the PD3, and the PD4 are arranged in a circular array, the first light-emitting unit 121 is located out of the area S in which the array is located, and the second light-emitting unit 123 is located in the center position of the array. That is, the second distances between the second light-emitting unit 123 and the PD1, the PD2, the PD3, and the PD4 are substantially equal to each other. The first distance between the first light-emitting unit 121 and the PD2 is substantially equal to the first distance between the first light-emitting unit 121 and the PD4.

Figures 9, 10:
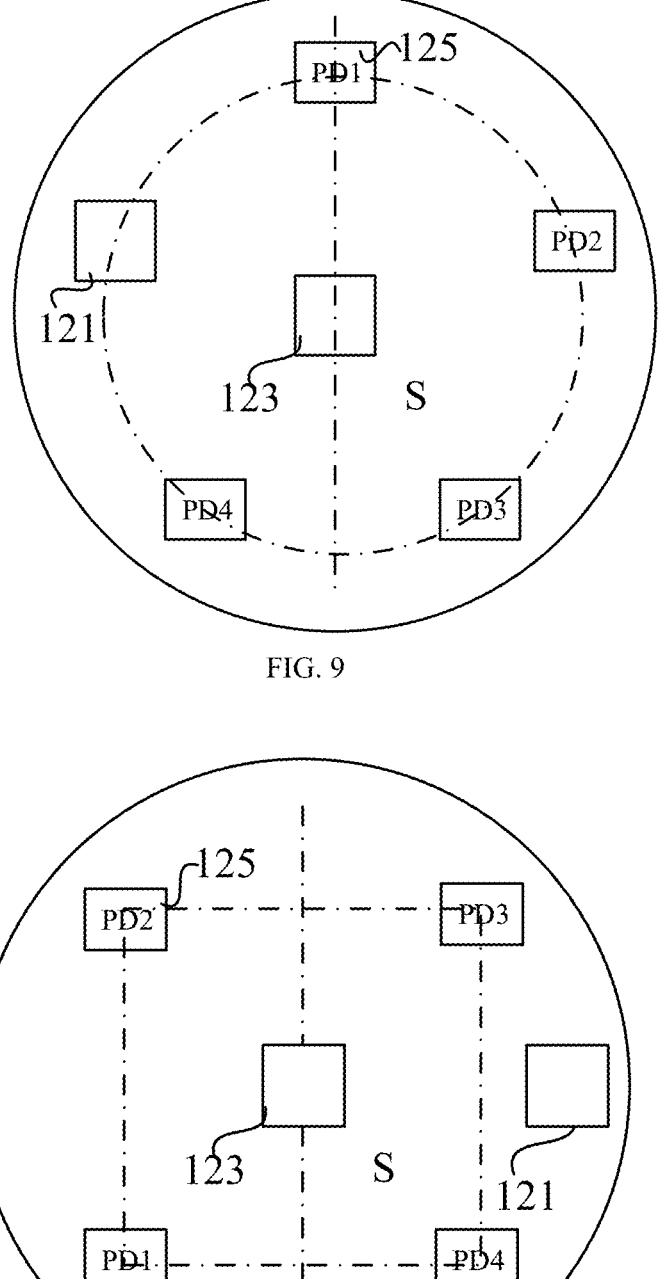
FIG. 9 is a schematic diagram illustrating a sixth frame structure of the PPG sensor in some embodiments of the present disclosure.
FIG. 10 is a schematic diagram illustrating a seventh frame structure of the PPG sensor in some embodiments of the present disclosure.

As shown in FIG. 9, in some embodiments, the first light-emitting unit 121 and the plurality of photoelectric sensors 125 are arranged in an array. The second light-emitting unit 123 is located in the center position of the array. That is, the first light-emitting unit 121 and each of the plurality of photoelectric sensors 125 are part of the array. The relative positions between the first light-emitting unit 121 and the plurality of photoelectric sensors 125 are not defined. The plurality of photoelectric sensors 125 include four photoelectric sensors 125, which may be respectively recorded as PD1, PD2, PD3, and PD4. The PD1, the PD2, the PD3, the PD4, and the first light-emitting unit 121 are arranged in a circular array. The second light-emitting unit 123 is located in the center position of the circular array. The distances between the second light-emitting unit 123 and the PD1, the PD2, the PD3, and the PD4 are substantially equal to each other. The distance between the first light-emitting unit 121 and PD2 is substantially equal to the distance between the first light-emitting unit 121 and PD4.

Figure 11:
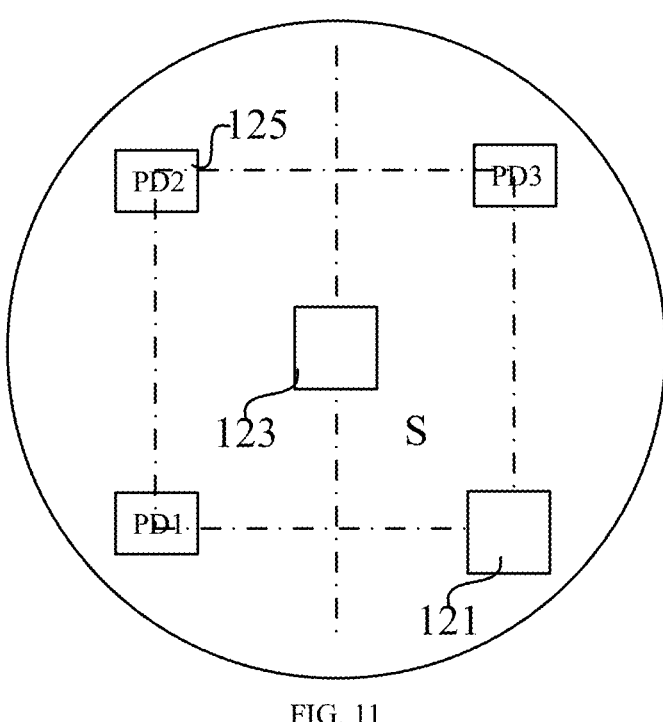
FIG. 11 is a schematic diagram illustrating an eighth frame structure of the PPG sensor in some embodiments of the present disclosure.

In some embodiments, as shown in FIG. 10, the plurality of photoelectric sensors 125 are arranged in an array, and the array may be a rectangular array or a circular array. In some embodiments, as shown in FIG. 11, the first light-emitting unit 121 and the plurality of photoelectric sensors 125 are arranged in an array, and the array may be a rectangular array or a circular array.

In some embodiments, the distance between the second light-emitting unit 123 and each of the PD1, the PD2, the PD3, and the PD4 is in a range of 4-5 mm. The distance between the first light-emitting unit 121 and each of PD1 and PD3 is in a range of 7-9 mm.

With respect to the PPG sensor shown in FIGS. 5-11, as the biological characteristics of the object to be detected are detected, the control module 127 may control the photoelectric sensors 125 of the first photoelectric sensor group to be connected in parallel to form the first measurement channel with the first light-emitting unit 121, and control the photoelectric sensors 125 of the second photoelectric sensor group to be connected in parallel to form the second measurement channel with the second light-emitting unit 123 in another scenario. The biological characteristics of the object to be detected may be detected based on the PPG signal acquired by the first measurement channel or the second measurement channel. The constructed first measurement channel and second measurement channel may be applied to different application scenarios, so as to extend or enlarge the application range of the PPG sensor. In addition, on condition that photocurrent information of the same degree is obtained, the measurement channel in which the photoelectric sensors are arranged in parallel may reduce the luminous brightness of the first light-emitting unit 121 or the second light-emitting unit 123 compared with the measurement channel in which the photoelectric sensors 125 are arranged independently. In this way, the drive current or drive voltage used to drive the first light-emitting unit 121 or the second light-emitting unit 123 may be reduced, the power consumption of the PPG sensor may be reduced, and the endurance time and service life of the PPG sensor may be improved.

11

12

Figure 12:
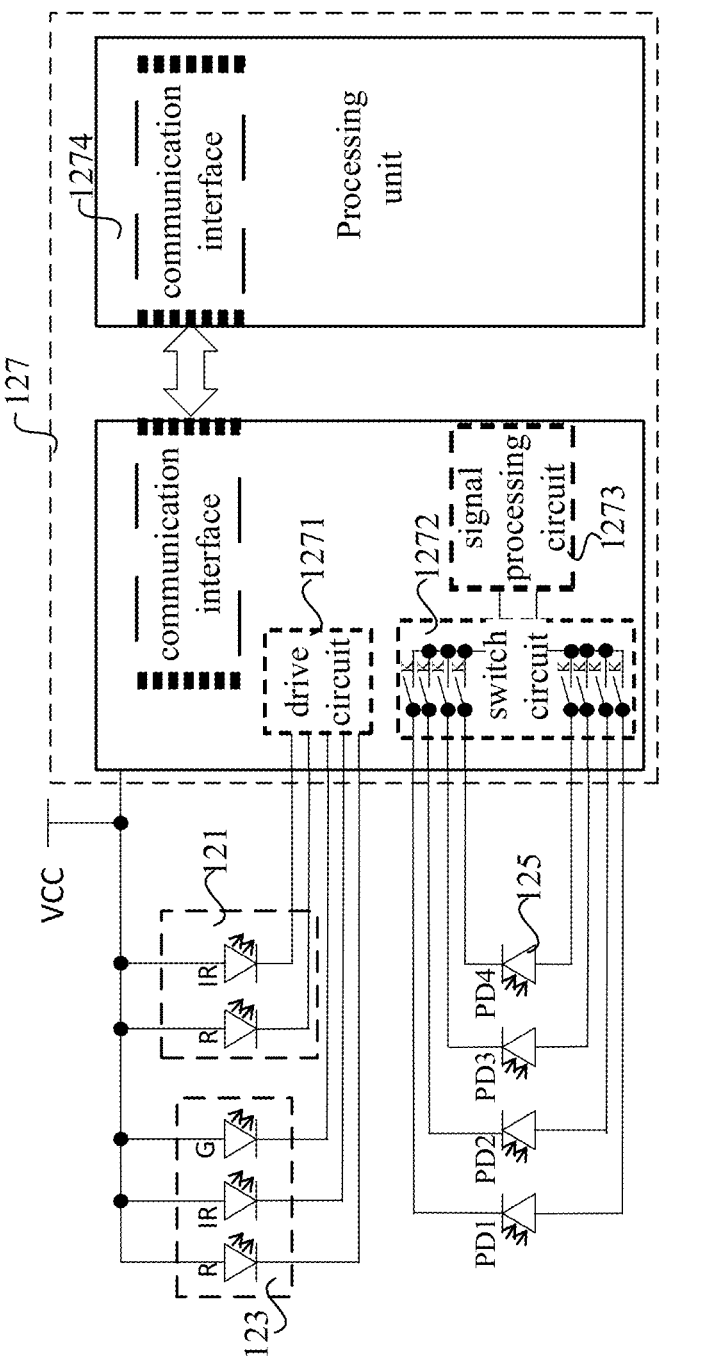
FIG. 12 is a schematic diagram illustrating a ninth frame structure of the PPG sensor in some embodiments of the present disclosure.

As shown in FIG. 12, in some embodiments, the control module 127 includes a drive circuit 1271, a switch circuit 1272, a signal processing circuit 1273, and a processing unit 1274. The drive circuit 1271 is connected to the first light-emitting unit 121 and the second light-emitting unit 123, and configured to drive the first light-emitting unit 121 to emit the first optical signal and drive the second light-emitting unit 123 to emit the another first optical signal. Each of the first optical signal and the another first optical signal may include at least one selected from the group consisting of red light and infrared light for detecting the blood oxygen saturation. In some embodiments, the drive circuit 1271 may also drive the second light-emitting unit 123 to emit the second optical signal. The second optical signal may include green light for detecting the heart-rate information. The drive circuit 1271 may drive the light emitting units to emit the first optical signal, the another first optical signal, or the second optical signal in a time-sharing mode according to the detection demand.

The switch circuit 1272 may be connected to each of the plurality of photoelectric sensors 125 and the signal processing circuit 1273 respectively, and configured to selectively conduct the detection channel in which a corresponding one of the plurality of photoelectric sensors 125 is located under the control of the signal processing circuit 1273.

As it is necessary to detect the blood-oxygen-saturation information of the object to be detected, the drive circuit 1271 may drive the first light-emitting unit 121 to emit the first optical signal, and the signal processing circuit 1273 may control the switch circuit 1272 to selectively conduct the detection channels in which M photodiodes in the first measurement channel are located to connect the M photodiodes in parallel, and generate the first PPG signal based on the photocurrent signal acquired by the first measurement channel. In addition, the drive circuit 1271 may drive the second light-emitting unit 123 to emit the another first optical signal, and the signal processing circuit 1273 may control the switch circuit 1272 to selectively conduct the detection channels in which N photodiodes in the second measurement channel are located to connect the N photodiodes in parallel, and generate the second PPG signal based on the photocurrent signal acquired by the second measurement channel.

In some embodiments, the switch circuit 1272 may include a plurality of switches K, and two switches K may control the detection channel in which one photoelectric sensor 125 is located. In some embodiments, one of the two switches K is arranged between the anode of the photoelectric sensor 125 and the signal processing circuit 1273, and the other of the two switches K is arranged between the cathode of the photoelectric sensor 125 and the signal processing circuit 1273. In some embodiments, in case that the number of the photoelectric sensors 125 is four, eight switches K may be arranged to control the detection channels in which the four photoelectric sensors 125 are located to be turned on or turned off.

It should be noted that, the specific form of the switch circuit 1272 is not limited by the embodiments of the present disclosure, and is not limited to the aforementioned embodiments.

The processing unit 1274 is connected to the signal processing circuit 1273, and configured to determine the target measurement channel according to the first PPG signal or the second PPG signal. In some embodiments, the processing unit 1274 may obtain a perfusion index (PI) according to the obtained first photocurrent signal or second photocurrent signal, and determine the target measurement channel according to the PI. The PI value reflects the condition of pulsatile blood flow (that is, the perfusion capacity of blood flow). The greater the pulsatile blood flow, the more the pulsatile component, and the greater the PI value. At a monitoring position, both pulsatile tissues (such as arteriole blood flow which is changing) and non-pulsatile tissues (such as venous blood, muscle, and other tissues) absorb light. The amount of the light absorbed by the pulsatile tissue is recorded as a pulsatile signal (AC). The amount of the light absorbed by the non-pulsatile tissue is recorded as a non-pulsatile signal (DC). The PI is a proportion of AC to DC in percentage (PI=AC/DC×100%). As the light passes through the skin tissue and then be reflected to the photoelectric sensor 125, the light has certain attenuation. The light absorbed by muscles, bones, veins and other connecting tissues is substantially unchanged, while the blood is different. Since there is blood flow in an artery, the light absorbed by the artery naturally changes. When the photoelectric sensor 125 converts the optical signal into an electrical signal, since the light absorbed by the artery changes while the light absorbed by other tissues is substantially unchanged, the obtained PPG signal may include a DC signal (which corresponds to the non-pulsatile signal) and an AC signal (which corresponds to the pulsatile signal). Therefore, the PI may be obtained based on the photocurrent signal.

The processing unit 1274 may determine the target measurement channel from the first measurement channel and the second measurement channel according to the obtained PI, and then control the target measurement channel to detect the blood-oxygen-saturation information of the object to be detected. In case that the PI is less than a preset threshold, the first measurement channel is taken as the target measurement channel. In case that the PI is greater than or equal to the preset threshold, the second measurement channel is taken as the target measurement channel. The PI value is proportional to the strength of the PPG signal. In some embodiments, the larger the PI value, the stronger the PPG signal. In case that the PPG signal is relatively strong, the second measurement channel with the low power-consumption level may be selected as the target measurement channel, in this way, not only the accuracy of measurement is ensured, but also the power consumption is taken into account. In case that the PPG signal is relatively weak, the first measurement channel with the high power-consumption level may be selected as the target measurement channel, in this way, the PPG signal with relatively good quality may be obtained, and the measurement accuracy may be improved.

After determining the target measurement channel, the processing unit 1274 may drive the first light-emitting unit 121 in the target measurement channel to emit the first optical signal or drive the second light-emitting unit 123 in the target measurement channel to emit the another first optical signal, and send a target drive signal to the signal processing circuit 1273 to control the photoelectric sensors 125 in the target measurement channel to be connected in parallel, so as to acquire the photocurrent signal. In this way, the corresponding PPG signal may be obtained, and the blood-oxygen-saturation information of the object to be detected may be detected.

In some embodiments, as it is necessary to detect the heart-rate information of the object to be detected, the drive circuit 1271 may drive the second light-emitting unit 123 to emit the second optical signal, and the signal processing circuit 1273 may control the switch circuit 1272 to conduct or turn on the detection channels in which the plurality of photoelectric sensors are located in a time-sharing mode. In this way, each of the plurality of photoelectric sensors may form a third measurement channel with the second light-emitting unit 123. That is, one independent photoelectric sensor may form one independent third measurement channel with the second light-emitting unit 123, so as to detect the heart-rate information of the object to be detected.

In some embodiments, the first light-emitting unit 121 may be the two-in-one LED assembly emitting the red light and the infrared light, the second light-emitting unit 123 may be the three-in-one LED assembly emitting the red light, the infrared light, and the green light, and the plurality of photoelectric sensors 125 include the PD1, the PD2, the PD3, and the PD4. Based on the first light-emitting unit 121, the second light-emitting unit 123, the PD1, the PD2, the PD3, and the PD4, the first measurement channel, the second measurement channel, and a plurality of third measurement channels (i.e., heart-rate measurement channels) may be constructed or formed. The photoelectric sensors 125 in the first measurement channel include the PD1 and the PD3. The distance between the first light-emitting unit 121 and the PD1 is substantially equal to the distance between the first light-emitting unit 121 and the PD3. The photoelectric sensors 125 in the second measurement channel include the PD1, the PD2, the PD3, and the PD4. The distances between the second light-emitting unit 123 and the PD1, the PD2, the PD3, and the PD4 are substantially equal to each other. The measurement channels are as follows.

The first measurement channel: the PD1 and the PD3 are connected in parallel, and then connected to the first light-emitting unit 121.

The second measurement channel: the PD1, the PD2, the PD3, and the PD4 are connected in parallel, and then connected to the second light-emitting unit 123.

The heart-rate measurement channel 1: the second light-emitting unit 123 is connected to the PD1.

The heart-rate measurement channel 2: the second light-emitting unit 123 is connected to the PD2.

The heart-rate measurement channel 3: the second light-emitting unit 123 is connected to the PD3.

The heart-rate measurement channel 4: the second light-emitting unit 123 is connected to the PD4.

With the arrangement of the first light-emitting unit 121, the second light-emitting unit 123, and the four photoelectric sensors 125 as aforementioned, the first measurement channel and the second measurement channel for measuring the blood oxygen saturation may be formed, and the plurality of third measurement channels for measuring the heart-rate information may also be formed. The PPG sensor may select different blood oxygen measurement channels for measurement according to different scenarios, so as to optimize the power consumption and performance. In some embodiments, in harsh environments such as low temperature (the lower the ambient temperature, the weaker the PPG signal of the human body), as the user needs to detect the blood oxygen saturation, the processing unit 1274 may control the first light-emitting unit 121 to emit the first optical signal, and control the PD1, the PD2, the PD3, and the PD4 to be connected in parallel to acquire the first photocurrent signal, and the blood oxygen saturation of the object to be detected may be obtained. That is, the first measurement channel with a relatively long distance may be used for a single measurement of the blood oxygen saturation. In this way, not only the accuracy of measurement is ensured, but also the power consumption is taken into account. In some embodiments, in continuously measuring the blood oxygen saturation during sleep (the PPG signal of the human body is relatively strong in this case), the processing unit 1274 may control the first light-emitting unit 121 to emit the first optical signal, and control the PD1 and the PD3 to be connected in parallel to acquire the second photocurrent signal. That is, the second measurement channel with the low power-consumption level is used for continuous measurement of the blood oxygen saturation. In this way, the blood oxygen saturation of the object to be detected may be obtained accurately, not only the accuracy of measurement is ensured, but also the power consumption is taken into account.

As it is necessary to detect the heart-rate information of the object to be detected, the drive circuit 1271 may drive the second light-emitting unit 123 in each heart-rate measurement channel to emit the second optical signal, control the PD1, the PD2, the PD3, and the PD4 to acquire the optical signal of the second light-emitting unit 123 separately in a time-sharing mode, and convert the second optical signal to a third photocurrent signal. The processing unit 1274 may obtain the PPG signal according to each of the third measurement channels, and a plurality of heart-rate detection results may be obtained. In this way, the heart-rate information of the object to be detected may be obtained. In some embodiments, the processing unit 1274 may obtain the average value of the plurality of heart-rate detection results, and determine the heart-rate information according to the average value, so as to improve the measurement accuracy of the heart-rate information.

The embodiments of the present disclosure also provide a PPG detection method. As shown in FIG. 13, in some embodiments, the PPG detection method includes operations 1302-1306.

Operation 1302, the method includes driving a first light-emitting unit to emit a first optical signal, and obtaining a first photocurrent signal by controlling M photoelectric sensors in a first measurement channel to be connected in parallel; or driving a second light-emitting unit to emit another first optical signal, and obtaining a second photocurrent signal by controlling N photoelectric sensors in a second measurement channel to be connected in parallel. N is greater than M, and both M and N are natural numbers greater than 1.

The drive circuit in the PPG sensor may be configured to drive the first light-emitting unit to emit the first optical signal and drive the second light-emitting unit to emit the another first optical signal. Each of the first optical signal and the another first optical signal may include at least one selected from the group consisting of red light and infrared light for detecting blood oxygen saturation. The first light-emitting unit 121 and the second light-emitting unit 123 may include one or more LEDs. In some embodiments, the one or more LEDs may include a red-light LED, an infrared-light LED, or a green-light LED. The plurality of photoelectric sensors 125 of the PPG sensor may be divided into a plurality of photoelectric sensor groups. The photoelectric sensors 125 in each of the plurality of photoelectric sensor groups may be connected in parallel. Each of the plurality of photoelectric sensor groups may form a measurement channel with the first light-emitting unit 121 or the second light-emitting unit 123 respectively, so as to detect the biological characteristics of the object to be detected. In some embodiments, the first light-emitting unit 121 and a first photoelectric sensor group may form a first measurement channel to obtain a first photocurrent signal. The first photoelectric sensor group may include M photoelectric sensors 125 connected in parallel. The second light-emitting unit 123 and a second photoelectric sensor group may form a second measurement channel to obtain a second photo-current signal. The second photoelectric sensor group may include N photoelectric sensors 125 connected in parallel. M is less than N, and both M and N are natural numbers greater than 1.

Operation 1304, the method includes determining a target measurement channel from the first measurement channel and the second measurement channel according to the obtained photocurrent signal.

The photocurrent signal obtained in the operation 1304 may be determined based on the operation 1302. In some embodiments, in case that the first photocurrent signal is obtained in the operation 1302, the photocurrent signal obtained in the operation 1304 is the first photocurrent signal. In case that the second photocurrent signal is obtained in the operation 1302, the photocurrent signal obtained in the operation 1304 is the second photocurrent signal.

Operation 1306, the method includes driving the target measurement channel to detect the biological characteristics of an object to be detected.

As the first light-emitting unit 121 is driven to emit the first optical signal, the PPG sensor may obtain the first PPG signal based on the first photocurrent signal acquired by the constructed first measurement channel. In some embodiments, as the second light-emitting unit 123 is driven to emit the second optical signal, the PPG sensor may obtain the second PPG signal based on the second photocurrent signal acquired by the constructed second measurement channel. The PPG sensor may determine the target measurement channel from the first measurement channel and the second measurement channel according to the PPG signal obtained by any one of the measurement channels, and control the target measurement channel to obtain the biological characteristics of the object to be detected, such as blood oxygen saturation, etc. In some embodiments, in case that the first measurement channel is currently controlled to work, that is, the first light-emitting unit 121 emits the first optical signal, and the M photoelectric sensors 125 in the first photoelectric sensor group is controlled to be connected in parallel to acquire the first photocurrent signal, whether the target measurement channel is the first measurement channel or the second measurement channel may be determined according to the first PPG signal obtained by the first measurement channel. In case that the target measurement channel is the first measurement channel, the first measurement channel is kept in a working state. In case that the target measurement channel is the second measurement channel, the second measurement channel is controlled to be in the working state. That is, the second light-emitting unit 123 is controlled to emit the another first optical signal, and the N photoelectric sensors 125 in the second photoelectric sensor group is controlled to be connected in parallel to acquire the second photocurrent signal. In this way, the PPG sensor may obtain the second PPG signal according to the second photocurrent signal to detect the blood oxygen saturation of the object to be detected.

The aforementioned PPG detection method may determine the target measurement channel based on the PPG signal obtained from the first measurement channel or the second measurement channel, and then control the target measurement channel to detect the biological characteristics of the object to be detected. Since the photoelectric sensors in each measurement channel are arranged in parallel with each other, the power consumption of the PPG sensor may be reduced. The number of the photoelectric sensors 125 connected in parallel in each of the measurement channels is different from the number of the photoelectric sensors 125 connected in parallel in another of the measurement channels, and the power-consumption levels corresponding to the measurement channels are also different from each other. The PPG sensor may determine the target measurement channel according to the first photocurrent signal or the second photocurrent signal currently acquired, so as to adapt to different detection scenarios. In some embodiments, in case that the PPG signal corresponding to the first photocurrent signal or the second photocurrent signal is relatively weak, the first measurement channel with a high-power-consumption level may be used to detect the biological characteristics. In case that the PPG signal corresponding to the first photocurrent signal or the second photocurrent signal is relatively strong, the second measurement channel with a low power-consumption level may be used to detect the biological characteristics. In this way, not only the accuracy of measurement is ensured, but also the power consumption is taken into account In some embodiments, the determining a target measurement channel from the first measurement channel and the second measurement channel according to the obtained photocurrent signal includes the following operations: obtaining a perfusion index (PI) according to the obtained photocurrent signal; taking the first measurement channel as the target measurement channel in response to the PI being less than a preset threshold; and taking the second measurement channel as the target measurement channel in response to the PI being greater than or equal to the preset threshold.

The PI value reflects the condition of pulsatile blood flow (that is, the perfusion capacity of blood flow). The greater the pulsatile blood flow, the more the pulsatile component, and the greater the PI value. At a monitoring position, both pulsatile tissues (such as arteriole blood flow which is changing) and non-pulsatile tissues (such as venous blood, muscle, and other tissues) absorb light. The amount of the light absorbed by the pulsatile tissue is recorded as a pulsatile signal (AC), the amount of the light absorbed by the non-pulsatile tissue is recorded as a non-pulsatile signal (DC), and the PI is a proportion of AC to DC in percentage (PI=AC/DC×100%). As the light passes through the skin tissue and then be reflected to the photoelectric sensor 125, the light has certain attenuation. The light absorbed by muscles, bones, veins and other connecting tissues is substantially unchanged, while the blood is different. Since there is blood flow in an artery, the light absorbed by the artery naturally changes. When the photoelectric sensor 125 converts the optical signal into an electrical signal, since the light absorbed by the artery changes while the light absorbed by other tissues is substantially unchanged, the obtained PPG signal may include a DC signal (which corresponds to the non-pulsatile signal) and an AC signal (which corresponds to the pulsatile signal). Therefore, the PI may be obtained based on the photocurrent signal.

The PI value is proportional to the strength of the PPG signal. In some embodiments, the larger the PI value, the stronger the PPG signal. In case that the PI is less than the preset threshold, the first measurement channel is taken as the target measurement channel. In case that the PI is greater than or equal to the preset threshold, the second measurement channel is taken as the target measurement channel. In case that the PPG signal is relatively strong, the second measurement channel with the low power-consumption level may be selected as the target measurement channel, in this way, not only the accuracy of measurement is ensured, but also the power consumption is taken into account. In case that the PPG signal is relatively weak, the first measurement channel with the high power-consumption level may be selected as the target measurement channel, in this way, the PPG signal with relatively good quality may be obtained, and the measurement accuracy may be improved.

In some embodiments, the PPG detection method also includes operations 1402-1406.

Operation 1402, the method includes driving the second light-emitting unit to emit a second optical signal, and obtaining a plurality of third photocurrent signals by controlling the plurality of photoelectric sensors in a time-sharing mode.

The second light-emitting unit 123 may also be configured to emit the second optical signal. The second optical signal may include green light for detecting the heart-rate information. The second light-emitting unit 123 may include one or more LEDs. In some embodiments, the one or more LEDs at least include a green-light LED.

The PPG sensor may drive the second light-emitting unit 123 to emit the second optical signal, and conduct or turn on the detection channels in which the plurality of photoelectric sensors are located in a time-sharing mode. In this way, each of the plurality of photoelectric sensors may form a third measurement channel with the second light-emitting unit 123, and convert the second optical signal into the corresponding third photocurrent signal. That is, one independent photoelectric sensor may form one independent third measurement channel with the second light-emitting unit 123, so as to detect the heart-rate information of the object to be detected.

Operation 1404, the method includes obtaining a heart-rate detection result according to each of the plurality of third photocurrent signals.

Operation 1406, the method includes detecting heart-rate information of the object to be detected according to the heart-rate detection result.

The PPG sensor may obtain a plurality of heart-rate detection results according to the PPG signals obtained by the plurality of third measurement channels, and then obtain the heart-rate information of the object to be detected. In some embodiments, the PPG sensor may obtain the average value of the plurality of heart-rate detection results, and determine the heart-rate information according to the average value, so as to improve the measurement accuracy of heart-rate information.

The aforementioned PPG detection method may not only detect the blood-oxygen-saturation information of the object to be detected, but also detect the heart-rate information of the object to be detected. The accuracy of heart-rate detection may be improved based on the plurality of heart-rate detection channels.

The embodiments of the present disclosure also provide a wearable device including a strap assembly and an electronic device described in any one of the aforementioned embodiments. The wearable device may measure the physiological parameter information of the human body, and the measurement accuracy is improved.

The aforementioned embodiments only express several embodiments of the present disclosure, and the descriptions are specific and detailed. However, the aforementioned embodiments cannot be understood as limiting the scope of the present disclosure. It should be pointed out that, without departing from the concept of the present disclosure, those skilled in the art may also make some changes and improvements, which are within the protection scope of the present disclosure. Therefore, the protection scope of the present disclosure shall be subject to the appended claims.

What is claimed is:

1. A photoplethysmography (PPG) sensor, comprising:
a first light-emitting unit;
a second light-emitting unit, wherein each of the first light-emitting unit and the second light-emitting unit is configured to emit a first optical signal;
a plurality of photoelectric sensors, wherein the first light-emitting unit and M photoelectric sensors of the plurality of photoelectric sensors form a first measurement channel, the M photoelectric sensors are connected in parallel, and a first photocurrent signal is obtained based on the first measurement channel; the second light-emitting unit and N photoelectric sensors of the plurality of photoelectric sensors form a second measurement channel, the N photoelectric sensors are connected in parallel, and a second photocurrent signal is obtained based on the second measurement channel; wherein N is greater than M, and less than or equal to the total number of the plurality of photoelectric sensors, and both M and N are natural numbers and
a control module, connected to the first light-emitting unit, the second light-emitting unit, and the plurality of photoelectric sensors respectively, and configured to determine a target measurement channel from the first measurement channel and the second measurement channel according to the first photocurrent signal or the second photocurrent signal received by the control module and control the target measurement channel to detect biological characteristics of an object to be detected;
wherein the first measurement channel has a power-consumption level higher than that of the second measurement channel; in a case where a strength of a PPG signal generated based on the first photocurrent signal or the second first photocurrent signal is less than a preset threshold, the first measurement channel is determined as the target measurement channel; and in a case where the strength of the PPG signal generated based on the first photocurrent signal or the second first photocurrent signal is greater than or equal to the preset threshold, the second measurement channel is determined as the target measurement channel.

2. The PPG sensor as claimed in claim 1, wherein a first distance is defined between the first light-emitting unit and each of the photoelectric sensors in the first measurement channel, and first distances corresponding to the photoelectric sensors in the first measurement channel are equal to each other, a second distance is defined between the second light-emitting unit and each of the photoelectric sensors in the second measurement channel, and second distances corresponding to the photoelectric sensors in the second measurement channel are equal to each other, wherein the first distance is greater than the second distance.

3. The PPG sensor as claimed in claim 2, wherein the plurality of photoelectric sensors are arranged along a same arc and spaced apart from each other, and both the first light-emitting unit and the second light-emitting unit are arranged on a same side of the arc; or
the plurality of photoelectric sensors are arranged along a same arc and spaced apart from each other, and the first light-emitting unit and the second light-emitting unit are arranged on different sides of the arc respectively.

4. The PPG sensor as claimed in claim 3, wherein the first light-emitting unit and the second light-emitting unit are arranged along a same straight line.

5. The PPG sensor as claimed in claim 2, wherein the plurality of photoelectric sensors are arranged in an array, the second light-emitting unit is located in a center position of the array, and the first light-emitting unit is arranged out of an area in which the array is located; or the first light-emitting unit and the plurality of photoelectric sensors are arranged in an array, and the second light-emitting unit is located in a center position of the array.

6. The PPG sensor as claimed in claim 5, wherein the array is a rectangular array or a circular array.

7. The PPG sensor as claimed in claim 1, wherein the M photoelectric sensors share one or more of the plurality of photoelectric sensors with the N photoelectric sensors.

8. The PPG sensor as claimed in claim 1, wherein in response to the control module driving the first light-emitting unit or the second light-emitting unit to emit the first optical signal, the control module is configured to control the target measurement channel to detect blood-oxygen-saturation information of the object to be detected.

9. The PPG sensor as claimed in claim 8, wherein the control module comprises:

a drive circuit, connected to the first light-emitting unit and the second light-emitting unit respectively, and configured to drive the first light-emitting unit or the second light-emitting unit to emit the first optical signal;

a switch circuit, connected to each of the plurality of photoelectric sensors, and configured to selectively conduct a detection channel in which a corresponding one of the plurality of photoelectric sensors is located;

a signal processing circuit, connected to the switch circuit, and configured to:

control the switch circuit to selectively conduct detection channels in which the M photodiodes in the first measurement channel are located and generate a first PPG signal based on the photocurrent signal acquired by the first measurement channel; or control the switch circuit to selectively conduct detection channels in which the N photodiodes in the second measurement channel are located and generate a second PPG signal based on the photocurrent signal acquired by the second measurement channel; and a processing unit, connected to the signal processing circuit, and configured to determine the target measurement channel according to the first PPG signal or the second PPG signal and send a target drive signal to the signal processing circuit according to the target measurement channel, wherein the target drive signal is configured to control the photoelectric sensors in the target measurement channel to be connected in parallel.

10. The PPG sensor as claimed in claim 9, wherein the drive circuit is configured to drive the second light-emitting unit to emit a second optical signal, and the signal processing circuit is configured to control the switch circuit to conduct detection channels in which the plurality of photoelectric sensors are located, to detect the heart-rate information of the object to be detected.

11. The PPG sensor as claimed in claim 10, wherein the switch circuit comprises a plurality of switches, and every two of the plurality of switches is configured to control the detection channel in which a corresponding one of the plurality of photoelectric sensors is located to be turned on or turned off.

12. The PPG sensor as claimed in claim 2, wherein the first distance is in a range of 7-9 mm, and the second distance is in a range of 4-5 mm.

13. A photoplethysmography (PPG) detection method, comprising:

driving a first light-emitting unit to emit a first optical signal, and obtaining a first photocurrent signal by controlling M photoelectric sensors in a first measurement channel to be connected in parallel; or driving a second light-emitting unit to emit the first optical signal, and obtaining a second photocurrent signal by controlling N photoelectric sensors in a second measurement channel to be connected in parallel; wherein N is greater than M, and both M and N are natural numbers;

determining a target measurement channel from the first measurement channel and the second measurement channel according to the first photocurrent signal or the second photocurrent signal, comprising: determining the first measurement channel as the target measurement channel in a case where a strength of a PPG signal generated based on the first photocurrent signal or the second first photocurrent signal is less than a preset threshold, and determining the second measurement channel as the target measurement channel in a case where the strength of the PPG signal generated based on the first photocurrent signal or the second first photocurrent signal is greater than or equal to the preset threshold; wherein the first measurement channel has a power-consumption level higher than that of the second measurement channel; and driving the target measurement channel to detect biological characteristics of an object to be detected.

14. The method as claimed in claim 13, wherein the determining a target measurement channel from the first measurement channel and the second measurement channel according to the first photocurrent signal or the second photocurrent signal comprises:

determining the target measurement channel from the first measurement channel and the second measurement channel according to a strength of the first photocurrent signal or a strength of the second photocurrent signal.

15. The method as claimed in claim 13, wherein the determining a target measurement channel from the first measurement channel and the second measurement channel according to the first photocurrent signal or the second photocurrent signal comprises:

obtaining a perfusion index (PI) according to first photocurrent signal or the second photocurrent signal;

taking the first measurement channel as the target measurement channel in response to the PI being less than a preset threshold; and taking the second measurement channel as the target measurement channel in response to the PI being greater than or equal to the preset threshold.

16. The method as claimed in claim 13, further comprising:

driving the second light-emitting unit to emit a second optical signal, and obtaining a plurality of third photocurrent signals by controlling the plurality of photoelectric sensors;

obtaining a heart-rate detection result according to each of the plurality of third photocurrent signals; and detecting heart-rate information of the object to be detected according to the heart-rate detection result.

17. An electronic device, comprising:

a housing, defining a detection window; and a photoplethysmography (PPG) sensor, exposed out of the housing from the detection window, wherein the PPG sensor comprises:

a first light-emitting unit;

a second light-emitting unit, wherein each of the first light-emitting unit and the second light-emitting unit is configured to emit red light and infrared light, and the second light-emitting unit is further configured to emit green light;

a plurality of photoelectric sensors, wherein the first light-emitting unit and M photoelectric sensors of the plurality of photoelectric sensors form a first measurement channel, the M photoelectric sensors are connected in parallel, and a first photocurrent signal is obtained based on the first measurement channel; the second light-emitting unit and N photoelectric sensors of the plurality of photoelectric sensors form a second measurement channel, the N photoelectric sensors are connected in parallel, and a second photocurrent signal is obtained based on the second measurement channel; wherein N is greater than M, and less than or equal to the total number of the plurality of photoelectric sensors, and both M and N are natural numbers; and a control module, connected to the first light-emitting unit, the second light-emitting unit, and the plurality of photoelectric sensors respectively, and configured to determine a target measurement channel according to the first photocurrent signal or the second photocurrent signal received by the control module and control the target measurement channel to detect biological characteristics of an object to be detected; and wherein the plurality of photoelectric sensors are arranged in an array, the second light-emitting unit is located in a center position of the array, and the first light-emitting unit is arranged out of an area in which the array is located.

18. The electronic device as claimed in claim 17, wherein a first distance is defined between the first light-emitting unit and each of the photoelectric sensors in the first measurement channel, and first distances corresponding to the photoelectric sensors in the first measurement channel are equal to each other, a second distance is defined between the second light-emitting unit and each of the photoelectric sensors in the second measurement channel, and second distances corresponding to the photoelectric sensors in the second measurement channel are equal to each other, wherein the first distance is greater than the second distance.

19. The electronic device as claimed in claim 17, wherein the array is a rectangular array or a circular array.

20. The electronic device as claimed in claim 17, wherein the control module comprises:

a drive circuit, connected to the first light-emitting unit and the second light-emitting unit respectively, and configured to drive the first light-emitting unit or the second light-emitting unit to emit the red light and the infrared light;

a switch circuit, connected to each of the plurality of photoelectric sensors, and configured to selectively conduct a detection channel in which a corresponding one of the plurality of photoelectric sensors is located;

a signal processing circuit, connected to the switch circuit, and configured to:

control the switch circuit to selectively conduct detection channels in which the M photodiodes in the first measurement channel are located and generate a first PPG signal based on the photocurrent signal acquired by the first measurement channel; or control the switch circuit to selectively conduct detection channels in which the N photodiodes in the second measurement channel are located and generate a second PPG signal based on the photocurrent signal acquired by the second measurement channel; and a processing unit, connected to the signal processing circuit, and configured to determine the target measurement channel according to the first PPG signal or the second PPG signal and send a target drive signal to the signal processing circuit according to the target measurement channel, wherein the target drive signal is configured to control the photoelectric sensors in the target measurement channel to be connected in parallel.

* * * * *